(12) United States Patent
Lloyd

(10) Patent No.: US 8,465,780 B2
(45) Date of Patent: Jun. 18, 2013

(54) BORATE MICRO EMULSION AND METHOD FOR MAKING THE SAME

(75) Inventor: Jeffrey Douglas Lloyd, Knoxville, TN (US)

(73) Assignee: Nisus Corporation, Rockford, TN (US)

( * ) Notice: Subject to any disclaimer, the term of this patent is extended or adjusted under 35 U.S.C. 154(b) by 461 days.

(21) Appl. No.: 12/708,739

(22) Filed: Feb. 19, 2010

(65) Prior Publication Data

US 2010/0147778 A1     Jun. 17, 2010

Related U.S. Application Data

(63) Continuation-in-part of application No. 12/271,954, filed on Nov. 17, 2008, which is a continuation-in-part of application No. 11/560,411, filed on Nov. 16, 2006.

(60) Provisional application No. 61/154,102, filed on Feb. 20, 2009.

(51) Int. Cl.
*A01N 59/14*     (2006.01)
*A61K 33/22*     (2006.01)

(52) U.S. Cl.
USPC ........... 424/660; 508/185; 423/276; 423/277; 423/298

(58) Field of Classification Search
USPC .......................................... 424/660; 508/185
See application file for complete search history.

(56) References Cited

U.S. PATENT DOCUMENTS

| | | | |
|---|---|---|---|
| 2,853,452 A | 9/1958 | Shock | |
| 2,998,310 A | 8/1961 | O'Brien | |
| 5,129,946 A | 7/1992 | Evans | |
| 5,785,939 A | 7/1998 | Schubert | |
| 6,022,480 A | 2/2000 | Girvan et al. | |
| 7,361,215 B2 | 4/2008 | Cobham | |
| 2001/0037035 A1 | 11/2001 | Kutcel | |
| 2003/0083217 A1 | 5/2003 | Kutcel | |
| 2003/0083218 A1 | 5/2003 | Kutcel | |

FOREIGN PATENT DOCUMENTS

| | | |
|---|---|---|
| FR | 2 890 394 A1 | 3/2007 |
| GB | 1 297 743 A1 | 11/1972 |
| WO | 9707062 A1 | 2/1997 |
| WO | 99/20565 | 4/1999 |
| WO | 00/23397 | 4/2000 |
| WO | 02/47876 A1 | 6/2002 |

OTHER PUBLICATIONS

Blasdale et al. (The solubility Curves of Boric Acid and the Borates of Sodium, JACS 61(4), Apr. 1939, pp. 917-920).*

* cited by examiner

*Primary Examiner* — Rebecca Prouty
*Assistant Examiner* — Danielle Sullivan
(74) *Attorney, Agent, or Firm* — Luedeka Neely Group, P.C.

(57) ABSTRACT

The specification discloses a borate microemulsion product. In one embodiment, the borate microemulsion includes from about 24 to about 32 weight percent emulsified sodium pentaborate; and from about 24 to about 32 weight percent particulate boric acid suspended therein. The microemulsion has a density of about 9.5 to about 10.5 pounds per gallon at about room temperature. In certain embodiments, the microemulsion has a viscosity of about 1200 to about 1520 at a temperature of from about 66° F. to about 70° F. In certain other embodiments, microemulsion has a viscosity of about 1000 to about 3000 at a temperature of from about 70° F. to about 75° F.

23 Claims, No Drawings

BORATE MICRO EMULSION AND METHOD FOR MAKING THE SAME

CROSS-REFERENCE TO RELATED APPLICATIONS

This application is a continuation-in-part of copending application Ser. No. 12/271,954, filed Nov. 17, 2008, which in turn is a continuation-in-part of copending application Ser. No. 11/560,411, filed Nov. 16, 2006. This application also claims the benefit of the earlier filing date of provisional application 61/154,102, filed Feb. 20, 2009.

FIELD

The present disclosure relates in general to water treatment technology and, in particular, to an algaecide and buffer for use in residential, community, and commercial swimming pools as well as other man made water enclosures. The present disclosure also relates to a borate-based microemulsion product suitable for use in the treatment of swimming pools and similar structures and to a method for making the borate-based micro emulsion product.

BACKGROUND

Conventionally, the growth of algae and other undesirable microorganisms in swimming pool waters has been suppressed by the use of halogen-based chemical additives. In particular, liquid or solid forms of chlorine-containing chemicals such as hypochlorous acid, hypochlorite salts, sodium dichloro-s-triazinetrione (dichlor), and trichloro-s-triazinetrione (trichlor) have been added to swimming pool waters as algaecides. While effective in reducing or preventing algae growth, these additives are lost relatively quickly due to evaporation and photo-degradation, i.e, light-induced decomposition. Moreover, chlorine-containing additives are typically corrosive to steel surfaces and may also be an irritant to the skin and eyes. Accordingly, it is desirable to use alternative swimming pool treatment chemicals in order to reduce or eliminate the need for treatment chemicals containing chlorine or other halogens as well as to mitigate some of the negative attributes of chlorine and other halogen pool chemicals.

Attempts have been made to use boron-containing chemicals, such as tetraborate salts (i.e., borax) and boric acid as alternative swimming pool treatment chemicals. However, these chemicals are problematic. They tend to form into solid blocks or lumps when contacted with water which sink to the bottom of a pool due to the relatively limited solubility of the chemicals, or they tend to float on top of the water and are aesthetically displeasing. Crusts or scaling may also form on the interior surfaces of the swimming pool as well. Further, boric acid is also corrosive to metal fixtures and fittings.

In addition, the use of boric acid in swimming pools has been found to promote the formation of hypochlorous acid, which is an eye irritant, if used in conjunction with chlorine-based treatment chemicals. Borax also exhibits problems with chlorine retention as it promotes the photo-degradation of sodium dichloro-s-triazinetrione (i.e., dichlor) when the two chemicals are used together to treat pool water.

Thus, there remains a continuing need for improved alternative swimming pool treatment chemicals.

SUMMARY

The above and other needs are met by a method for reducing the rate of growth of algae in an enclosed volume of water, such as a swimming pool. The method includes the steps of providing a volume of water within a man made vessel and dissolving a treatment composition into the volume of water in an amount sufficient to reduce the rate of growth of algae in the water. The treatment composition includes a chlorine-containing sanitizer and a buffer, for instance an algaecidal buffer, which comprises a borate salt. When dissolved in the water, the treatment composition buffers the pH in a range from about 6.5 to about 8.8.

In one embodiment of the present disclosure, the algaecidal buffer preferably includes a salt selected from the group consisting of salts of octaborate, salts of pentaborate, salts of hexaborate and mixtures thereof. Suitable salts may include, for instance, sodium salts, potassium salts, lithium salts, magnesium salts, calcium salts, zinc salts, and mixtures thereof. Particularly preferred are sodium or potassium salts including disodium octaborate salt, sodium pentaborate salt, and sodium hexaborate. In certain embodiments, the treatment composition consists essentially of the chlorine-containing sanitizer and the algaecidal buffer. In still further embodiments, the treatment composition consists of only the chlorine-containing sanitizer and the algaecidal buffer.

In certain embodiments, the amount of algaecidal buffer dissolved in the volume of water is preferably from about 0.01 weight % to about 0.5 weight %, of algaecidal buffer in pool water. However, in certain other embodiments of the present disclosure, the amount of algaecidal buffer dissolved in the volume of water is preferably from about 0.001 weight % to about 0.1 weight %, of algaecidal buffer in pool water, and more preferably from about 0.02 weight % to about 0.05 weight %.

Advantageously, as compared to prior art boron-containing additives, it has been found that the salts of octaborate, pentaborate, and hexaborate used in the present dissolve more readily into the water and without the formation of crusts or scaling or floating debris or dust when contacted with water. When added to the water in a solid form, the time until the algaecidal buffer of the present disclosure is substantially dissolved in the volume of water is preferably from about 0.1 to about 50 minutes.

After the algaecidal buffer is dissolved, the water generally has a pH of from about 6.5 to about 8.8. In certain embodiments, the water preferably has a pH of from about 6.5 to about 8.4, more preferably from about 7 to 8, and most preferably from about 7.2 to about 7.6. This pH range is believed to be generally ideal for the operation and maintenance of the pool.

In certain embodiments of the present disclosure, the method of the present disclosure preferably further includes dissolving an effective amount of a sanitizer into the volume of water, wherein the sanitizer is selected from the group consisting of chlorine-containing sanitizers, bromine-containing sanitizers, silver-containing sanitizers, zinc-containing sanitizers, copper-containing sanitizers, quaternary ammonium-compound containing sanitizers, ozone sanitizers, UV sanitizers, and mixtures thereof.

More preferably, the sanitizer includes chlorine-containing sanitizers selected from the group consisting of chlorine gas, hypochlorite salts, sodium dichloro-s-triazinetrione (dichlor), and trichloro-s-triazinetrione (trichlor), and the amount of sanitizer dissolved in the volume of water is sufficient to provide from about 0.1 to about 10 ppm of free chlorine ($Cl^{-ve}$) in the pool water. The amount of sanitizer used is substantially reduced as compared to prior art usages of such sanitizers in the absence of salts of octaborate, pentaborate, and hexaborate added as an algaecidal buffer.

In general, the water, after the algaecidal buffer is dissolved therein, may remain substantially free of algae for at least about 7 days.

In another aspect, the present disclosure provides an algae-resistant water vessel such as a swimming pool. The algae-resistant water vessel includes a volume of water contained within a man-made vessel and a treatment composition dissolved in the volume of water in an amount sufficient to reduce the rate of growth of algae in the water, wherein the treatment composition includes a chlorine-containing sanitizer and a buffer such as an algaecidal buffer. The buffer in turn includes a borate salt. When dissolved in the water, the treatment composition generally buffers the pH in a range of from about 6.5 to about 8.8. In certain embodiments, the water preferably has a pH of from about 6.5 to about 8.4, more preferably from about 7 to 8, and most preferably from about 7.2 to about 7.6.

In one embodiment of the present disclosure, the algaecidal buffer preferably includes a salt selected from the group consisting of salts of octaborate, salts of pentaborate, salts of hexaborate and mixtures thereof. Suitable salts may include, for instance, sodium salts, potassium salts, lithium salts, magnesium salts, calcium salts, zinc salts, and mixtures thereof. Particularly preferred are sodium or potassium salts including disodium octaborate salt odium pentaborate salt, and sodium hexaborate. In certain embodiments, the treatment composition consists essentially of the chlorine-containing sanitizer and the algaecidal buffer. In still further embodiments, the treatment composition consists of only the chlorine-containing sanitizer and the algaecidal buffer In still another aspect, the present disclosure provides a method for reducing the rate of growth of algae in swimming pools. According to the method a volume of water is provided within a swimming pool. A borate salt selected from the group consisting of salts of octaborate, salts of pentaborate, salts of hexaborate and mixtures thereof is dissolved in the volume of water in an amount sufficient to provide a concentration of borate salt dissolved in the water of from about 0.01 weight % to about 0.5 weight %. A sanitizer is selected from the group consisting of hypochlorite salts, sodium dichloro-s-triazinetrione, and trichloro-s-triazinetrione is also dissolved in the volume of water in an amount sufficient to provide from about 0.1 ppm to about 10 ppm of free chlorine in the water.

In a further aspect, the present disclosure provides a method for making a borate microemulsion. According to one embodiment, the method includes mixing one part, by weight, acidic borate with from about 0.6 to about 1.4 parts, by weight, alkali borate and from about 1.5 to about 3 parts, by weight, water to form a first mixture. The first mixture is reacted at a temperature of from about 32° F. to about 212° F. to provide a first reaction product which comprises emulsified sodium pentaborate. More preferably, the first mixture is reacted at a temperature of from about 40° F. to about 100° F. The first reaction product is then mixed with an additional from about 0.5 to about 4 parts, by weight, acidic borate and from about 0.5 to about 2 parts, by weight, water to provide a second product which comprises emulsified sodium pentaborate and particulate boric acid suspended therein.

In certain embodiments according to the present disclosure, the acidic borate preferably includes a borate selected from the group consisting of orthoboric acid, metaboric acid, boric oxide, and mixtures thereof.

In certain embodiments according to the present disclosure, the alkali borate preferably includes a borate selected from the group consisting of sodium borates, potassium borates, lithium borates, and mixtures thereof. More preferably, the alkali borate includes a borate selected from the group consisting of tincal, kernite, anhydrous sodium tetraborate, sodium tetraborate pentahydrate, sodium tetraborate decahydrate, and mixtures thereof. Alternatively, the alkali borate may include borate selected from the group consisting of ulexite, colemanite, and mixtures thereof.

In certain embodiments, the first reaction product preferably includes from about 25 to about 75 weight percent emulsified sodium pentaborate. The second product preferably includes from about 18 to about 38 weight percent emulsified sodium pentaborate and from about 18 to about 38 weight percent particulate boric acid. More preferably, the second product includes from about 24 to about 32 weight percent emulsified sodium pentaborate and from about 24 to about 32 weight percent particulate boric acid.

In some embodiments, the second product preferably includes from about 8 to about 13 weight percent elemental boron. In one embodiment, the second product more preferably includes about 11.5 weight percent elemental boron. In another embodiment, the second product more preferably includes about 10 weight percent elemental boron.

In certain embodiments, the viscosity of the second product is preferably from about 1000 to about 2000 centipoise at a temperature of from about 64° F. to about 72° F. More preferably, the viscosity of the second product is from about 1200 to about 1520 centipoise at a temperature of from about 66° F. to about 70° F. In certain other embodiments, the viscosity of the second product is preferably from about 1000 to about 3000 centipoise at a temperature of from about 70° F. to about 75° F. More preferably, the viscosity of the second product is from about 2000 to about 2800 centipoise at a temperature of from about 70° F. to about 75° F.

In certain embodiments according to the present disclosure, the second product preferably has a density of from about 9 to about 11 pounds per gallon at about room temperature. More preferably, the second product has a density of from about 9.5 to about 10.5 pounds per gallon at about room temperature.

The pH of the second product preferably ranges from about 6 to about 7.5 in certain embodiments. More preferably, the pH of the second product preferably ranges from about 6.5 to about 7.

In still another aspect, the present disclosure provides a method for making a borate microemulsion, including at least the steps of: mixing one part, by weight, boric acid with from about 0.6 to about 1.4 parts, by weight, sodium tetraborate and from about 1.5 to about 3 parts, by weight, water to form a first mixture; reacting the first mixture at a temperature of from about 40° F. to about 100° F. to provide a first reaction product which comprises emulsified sodium pentaborate; and mixing the first reaction product with an additional from about 0.5 to about 4 parts, by weight, boric acid and from about 0.5 to about 2 parts, by weight, water to provide a second product which comprises emulsified sodium pentaborate and particulate boric acid suspended therein.

In certain embodiments, the sodium tetraborate preferably includes sodium tetraborate pentahydrate. Also, in certain embodiments, the boric acid preferably includes orthoboric acid.

In some embodiments, the density of the second product is more preferably about 10.2 pounds per gallon at about room temperature. In addition, in some embodiments, the pH of the second product is more preferably from about 6.7 to about 6.9.

In certain embodiments, the additional boric acid mixed with the first reaction product preferably includes powdered boric acid.

In some embodiments, the first mixture is preferably reacted in a high shear mixer or a ribbon blender. In addition, the additional boric acid is preferably mixed with the first reaction product using an inline mill.

The present disclosure also provides a borate microemulsion product. In one embodiment, the borate microemulsion includes from about 24 to about 32 weight percent emulsified sodium pentaborate; and from about 24 to about 32 weight percent particulate boric acid suspended therein. The microemulsion has a density of about 9.5 to about 10.5 pounds per gallon at about room temperature. In certain embodiments, the microemulsion has a viscosity of about 1200 to about 1520 at a temperature of from about 66° F. to about 70° F. In certain other embodiments, microemulsion has a viscosity of about 1000 to about 3000 at a temperature of from about 70° F. to about 75° F.

In certain embodiments according to the present disclosure, the density of the microemulsion is more preferably about 10.2 pounds per gallon at about room temperature.

In some embodiments, the pH of the microemulsion is preferably from about 6.5 to about 7. More preferably, the pH of the microemulsion is preferably from about 6.7 to about 6.9.

The borate microemulsion may be diluted with water. In certain embodiments, the microemulsion has a pH of from about 7.0 to about 8.0 after dilution in water at a rate of about 1 gallon microemulsion per 1000 gallons water. More preferably, the microemulsion has a pH of from about 7.2 to about 7.9 after dilution in water at a rate of about 1 gallon microemulsion per 1000 gallons water.

In certain embodiments, the borate microemulsion also preferably includes an anti-settling agent selected from the group consisting of xanthan gum, polyacrylates, acrylic acid, agar, carboxymethyl cellulose, clay, and mixtures thereof.

In still another aspect, the present disclosure provides a method for buffering the pH of a swimming pool. In one embodiment, the method includes preparing a borate microemulsion concentrate which includes from about 24 to about 32 weight percent emulsified sodium pentaborate; and from about 24 to about 32 weight percent particulate boric acid suspended therein. The borate microemulsion concentrate is then added to the water of a swimming pool in a ratio of from about 0.1 to about 1 gallons of concentrate per 1000 gallons of swimming pool water. The borate microemulsion concentrate has an initial pH of from about 6 to about 7.5 and after mixing with the swimming pool water provides a final pool water pH of from about 7.2 to about 7.9.

In certain preferred embodiments, the swimming pool includes a pool skimmer device and the borate microemulsion concentrate is mixed with the swimming pool water using the pool skimmer device. Advantageously, this addition of the borate microemulsion concentrate does not clog the pool skimmer device.

The present disclosure also provides a method for making a borate microemulsion with only a single reaction step. In one embodiment, the method includes the step of mixing one part, by weight, of an alkali borate is mixed with from about 1 to about 15 parts, by weight, of an acidic borate and from about 1 to about 20 parts, by weight, water to form a mixture; and the step of reacting the mixture at a temperature of from about 32° F. to about 212° F. to provide a reaction product which comprises emulsified sodium pentaborate and particulate boric acid suspended therein. Preferably, the reaction is carried out in a mixing vessel with a recirculation loop in order to improve the mixing efficiency.

In a more preferred embodiment, one part, by weight, of an alkali borate is mixed with from about 2 to about 5 parts, by weight, of an acidic borate and from about 2 to about 10 parts, by weight, water to form a mixture.

In certain embodiments according to the present disclosure, the acidic borate preferably includes a borate selected from the group consisting of orthoboric acid, metaboric acid, boric oxide, and mixtures thereof.

In certain embodiments according to the present disclosure, the alkali borate preferably includes a borate selected from the group consisting of sodium borates, potassium borates, lithium borates, and mixtures thereof. More preferably, the alkali borate includes a borate selected from the group consisting of tincal, kernite, anhydrous sodium tetraborate, sodium tetraborate pentahydrate, sodium tetraborate decahydrate, and mixtures thereof. Alternatively, the alkali borate may include borate selected from the group consisting of ulexite, colemanite, and mixtures thereof.

In certain embodiments, the reaction product preferably includes from about 18 to about 38 weight percent emulsified sodium pentaborate and from about 18 to about 38 weight percent particulate boric acid. More preferably, the reaction product includes from about 24 to about 32 weight percent emulsified sodium pentaborate and from about 24 to about 32 weight percent particulate boric acid.

In some embodiments, the reaction product preferably includes from about 8 to about 13 weight percent elemental boron. In one embodiment, the reaction product more preferably includes about 11.5 weight percent elemental boron. In another embodiment, the reaction product more preferably includes about 10 weight percent elemental boron.

In yet another aspect, the present disclosure provides a method for making a borate microemulsion, which includes the steps of: mixing one part, by weight, alkali borate with from about 1 to about 20 parts, by weight, of a non-borate acid and from about 1 to about 20 parts, by weight, water to form a mixture; and reacting the mixture at a temperature of from about 32 of to about 212 of to provide a reaction product which comprises from about 18 to about 38 weight percent emulsified sodium pentaborate and from about 18 to about 38 weight percent particulate boric acid suspended therein.

In certain embodiments, the alkali borate preferably includes a borate selected from the group consisting of tincal, kernite, anhydrous sodium tetraborate, sodium tetraborate pentahydrate, sodium tetraborate decahydrate, and mixtures thereof. More preferably, the alkali borate includes sodium tetraborate pentahydrate.

In certain embodiments, the non-borate acid preferably includes an acid selected from the group consisting of sulfuric acid, sulphur dioxide, sodium bisulphate, potassium bisulphate hydrochloric acid, chlorine, hypochlorous acid, carbon dioxide, carbonic acid, phosphoric acid, and mixtures thereof.

In other embodiments, the non-borate acid preferably includes an organic acid selected from the group consisting of carboxylic acids, dicarboxylic acids, sulfonic acids, and mixtures thereof.

In still another aspect, the present disclosure provides a method for making a borate microemulsion, which includes the steps of: mixing one part, by weight, acidic borate with from about 0.05 to about 2 parts, by weight, of a non-borate base and from about 1 to about 3 parts, by weight, water to form a mixture; and reacting the mixture at a temperature of from about 32 of to about 212 of to provide a reaction product which comprises from about 18 to about 38 weight percent emulsified sodium pentaborate and from about 18 to about 38 weight percent particulate boric acid suspended therein.

In certain embodiments, the acidic borate includes a borate selected from the group consisting of orthoboric acid, metaboric acid, boric oxide, and mixtures thereof. More preferably, the acidic borate includes orthoboric acid.

In certain embodiments, the non-borate base includes a base selected from the group consisting of sodium hydroxide, potassium hydroxide, calcium hydroxide, magnesium hydroxide, lithium hydroxide, sodium oxide, potassium oxide, calcium oxide, magnesium oxide, lithium oxide, sodium carbonate, potassium carbonate, calcium carbonate, magnesium carbonate, lithium carbonate, and mixtures thereof. More preferably, the non-borate base includes sodium hydroxide. In other embodiments, the non-borate base may include an organic base such as a primary amine, a secondary amine, or a tertiary amine.

DETAILED DESCRIPTION

In a first aspect, the present disclosure provides a method for reducing the rate of growth of algae in a volume of water such as a swimming pool. According to the method, an effective amount of a treatment composition which includes a chlorine-containing sanitizer and a buffer, generally an algaecidal buffer is dissolved into the volume of water to treat the water, to reduce the growth of algae in the water and to maintain a given pH range. As used in this context, the term "algaecidal" refers to and includes both compositions which are capable of killing algae and compositions which are capable of suppressing the further growth of algae.

The treatment may be used with any type of man made swimming pool or other body of water having a volume of water which is retained within a man made vessel. As used herein, "swimming pools" includes in-ground swimming pools, above-ground swimming pools, indoor swimming pools, and diving and wading pools, as well as hot tubs. The pool water may be retained by, for instance, cement or concrete walls, metal walls, tiled walls, plastic walls (such as polyethylene or glass reinforced polymer (GRP)), or a swimming pool liner formed of polymeric film such as vinyl. The treatment method may be used with all sizes of pools which are large enough to allow a human being to swim or bath therein.

The treatment may also be used to treat fire storage and sprinkler tanks, closed loop cooling systems, and open loop cooling systems such as those used in industrial cooling towers. In addition, the treatment may also be effective in other man made bodies of water such as water features, water fountains, water slides, and theme park water rides such as "log flumes." For convenience, however, the use of the treatment is described herein with respect to a swimming pool.

The algaecidal buffer utilized in the treatment composition and method of the disclosure is selected from the group of salts of octaborate, salts of pentaborate, salts of hexaborate and mixtures thereof. Suitable salts may include, for instance, sodium salts, potassium salts, lithium salts, magnesium salts, calcium salts, zinc salts, and mixtures thereof. Particularly preferred algaecidal buffer salts include potassium and sodium salts, such as disodium octaborate salt ($Na_2B_8O_{13}$) and sodium pentaborate salt ($NaB_5O_8$) as well as sodium hexaborate ($Na_2B_6O_{11}$). This includes both anhydrous forms of the salts as well as their hydrates, as well as different salts with different cations such as disodium octaborate tetrahydrate ($Na_2B_8O_{13} \times 4H_2O$), potassium pentaborate tetrahydrate ($KB_5O_8 \times 4H_2O$), sodium hexaborate tetrahydrate ($Na_2B_6O_{10} \times 4H_2O$) and sodium hexaborate decahydrate ($Na_2B_6O_{10} \times 10H_2O$).

Surprisingly, it has been found that the aforementioned octaborate, pentaborate, and hexaborate salts provide superior performance as algaecidal buffers as compared to other boron-containing compounds such as sodium tetraborate, i.e., borax ($Na_2B_4O_7$), and boric acid ($H_3BO_3$).

The pentaborate, octaborate, and/or hexaborate salts are added to the pool water in an amount which is effective to substantially suppress or eliminate algal growth within the pool water. In certain embodiments of the present disclosure, it has been found that dissolution of from about 0.01 to about 0.5 weight % of algaecidal buffer in pool water is sufficient for this purpose. More preferably, the amount of algaecidal buffer dissolved in the volume of pool water is preferably from about 0.025 to about 0.1 weight % in pool water. Thus, in a 10,000 gallon pool for example, from about 10 to about 500 pounds of the algaecidal buffer is generally added to the pool water. More preferably from about 25 to about 100 pounds of the algaecidal buffer is added to the pool water. However, in certain other embodiments of the present disclosure, the amount of algaecidal buffer dissolved in the volume of water is preferably from about 0.001 weight % to about 0.1 weight %, of algaecidal buffer in pool water, and more preferably from about 0.02 weight % to about 0.05 weight %.

The algaecidal buffer is preferably added directly to the pool as a dry bulk powder or granules. The powder or granules may in some instances be produced by spray drying or by granulation to form a dry flowable material. Formation of the powder by spray drying advantageously leads to an amorphous non-crystalline structure. This has been found to improve the immediate dispersion of the powder when added to water as well as the overall dissolution rate of the powder in the water.

However, the algaecidal buffer may alternatively be added as a liquid concentrate if desired or as a slowly dissolving solid block. In one embodiment, for instance, the algaecidal buffer may be provided as a micellar emulsion including from about 30 to about 60 weight percent borates, more preferably from about 45 to about 55 weight percent borates, dispersed in an aqueous suspension. In certain embodiments, the emulsion includes approximately 10 weight percent elemental boron. The algaecidal buffer may preferably be added to various locations about the pool to promote treatment of the entirety of the volume. Alternatively, the algaecidal buffer may be added in a single location within the pool. The buffer may also be added directly to a pool skimmer associated with a pool filtration system so as to use the pool pump and filter system to aid in dissolving and distributing the buffer within the pool. This is contrast to borates such as sodium tetraborate which cannot be added to the skimmer due to problems with clumping and reaction to form a solid mass that can block the skimmer system.

The pentaborate, octaborate, and/or hexaborate salts used in the present disclosure have been found to exhibit very good aqueous solubility and thus the algaecidal buffer powder or granules rapidly disperse and dissolve in the pool water. In general, the algaecidal buffer of the present disclosure is substantially dissolved in the volume of pool water in from about 0.1 to about 50 minutes, and more preferably from about 1 to about 5 minutes. When added to the pool water, the algaecidal buffer salts tend to disperse before reaching the bottom of the pool. In most instances, the algaecidal buffer salts of the present disclosure have been observed to completely dissolve prior to reaching the pool bottom. This is in decided contrast to the use of sodium tetraborate and/or boric acid which have lower aqueous solubilities and tend to form solid clumps in the pool water and/or encrustations on the inner surfaces of the swimming pool, or unsightly surface floating deposits.

Several benefits and advantages are provided due to the improved dissolution of the algaecidal buffer salts of the present disclosure. Caking and/or clumping of the buffer salts is substantially eliminated. This in turn means that clogging or blockages of swimming pumps and skimmers is also greatly reduced.

In addition, it has also been observed that scale formation on both metal and non-metal surfaces within the swimming pool is significantly reduced. In some instances, corrosion of metal surfaces may also be reduced.

In the past, the addition of chlorine additives to pool water, as well of use of the water by swimmers, has been found to lead to a decrease of pool water pH into an acidic range and to the formation of hypochlorous acid, which acts as an eye and skin irritant. Use of the buffers of the present disclosure has also been found to reduce the formation of hypochlorous acid in the pool water and to limit the associated drop in pH. Consequently, eye and skin irritation from the water is substantially reduced.

In some embodiments of the present disclosure, treatment of the pool water with salts of pentaborate, octaborate and/or hexaborate may be sufficient to substantially suppress or eliminate algal growth without use of any further treatment chemicals. In other embodiments of the disclosure, however, it may be desirable to combine treatment of the pool water using the aforementioned salts with a further treatment step of dissolving an effective amount of an additional sanitizer into the volume of pool water.

For example, effective algaecidal treatment results may be achieved by including as an additional treatment agent a sanitizer such as chlorine-containing sanitizers, bromine-containing sanitizers, silver-containing sanitizers, zinc-containing sanitizers, copper containing sanitizers, quaternary ammonium-containing sanitizers, ozone sanitizers, UV sanitizers and mixtures thereof. Particular chlorine-containing sanitizers include chlorine gas (which may for example be prepared by electrolysis of sodium chloride), sodium hypochlorite, calcium hypochlorite; lithium hypochlorite, sodium dichloro-s-triazinetrione (dichlor), and trichloro-s-triazinetrione (trichlor). It is particularly preferred to use either dichlor, trichlor, or a hypochlorite salt as an additional treatment agent.

When used in conjunction with salts of pentaborate and/or octaborate, according to the present disclosure, the amount of additional sanitizer dissolved in the volume of pool water is generally sufficient to provide from about 0.1 to about 10 ppm of free chlorine ($Cl^{-ve}$) in the pool water. For calcium hypochlorite, for example, the amount dissolved in the volume of pool water is preferably sufficient to provide from about 0.1 to about 0.5 ppm free chlorine in the pool water. The free chlorine level is not necessarily maintained at this level continuously, but it is preferred that the free chlorine level be maintained at this level at routine intervals in order to remove organic contamination in the water by oxidization as well as to kill pathogenic organisms.

In certain embodiments of the present disclosure, the treatment composition consists essentially of the chlorine-containing sanitizer and the algaecidal buffer. That is, the treatment composition does not any other additives which would have a substantial effect on the pH of the water being treated. In still further embodiments, the treatment composition consists of only the chlorine-containing sanitizer and the algaecidal buffer The swimming pool treatment according to the present disclosure has been found to remain effective in suppressing algae growth for extended periods of time without additional treatment. Moreover, the swimming pool treatment according to the present disclosure has been found to extend the effective lifespan of chlorine-containing sanitizers when added to pool water and thereby reduce the frequency at which such sanitizers must be replenished in the pool water.

Conventionally, chlorine-containing sanitizers tend to be rapidly removed from pool water due to photochemical degradation. If the chlorine-containing sanitizers are not promptly replaced, the pool will then be susceptible to the rapid and devastating growth of algal blooms in a short period of time. For example, conventionally used chlorine-containing sanitizers may be depleted and large algal blooms may develop, while a home owner is away on a relatively short summer vacation. If this occurs, very large acute doses of shock chlorine will then be needed to kill and remove the algae by oxidation, and the pool will be unsuitable for use until the algae is removed and the level of free chlorine in the pool returns to a safe level.

When chlorine-containing sanitizers are used in conjunction with the present disclosure, however, the rate of photodegradation of the chlorine has been found to be greatly reduced. The buffer salts of the invention also directly inhibit the growth of algae and bacteria. The intervals at which the sanitizers must be replenished are thus greatly extended. For example, an application once per week or even once per month can be satisfactory in a pool that previously had required applications once every few days.

Conventionally, pool water, after a chlorine-containing sanitizer is dissolved therein, may remain substantially free of algae for at least about 7 days. When an algaecidal buffer is combined with a chlorine-containing sanitizer, as according to one embodiment of the present disclosure, it has been found that pool water so treated may remain substantially free of algae for up to about 3 months. When the two are combined and the chlorine-containing sanitizer is replenished on a periodic basis, pool water so treated has been found to remain substantially free of algae for over 3 years and may continue to remain substantially fee of algae indefinitely.

As a further benefit of the swimming pool treatment of the present disclosure, it has been observed that dissolution of a pentaborate, octaborate and/or hexaborate salt algaecidal buffer in the pool water, in combination with a sanitizer, acts as a pH buffer for the swimming pool water.

Specifically, when an effective amount of from about 0.001 weight % to about 0.1 weight % (and more preferably from about 0.02 weight % to about 0.005 weight %) of the algaecidal buffer is dissolved in the pool water, the pH of the pool water is buffered in a range of from about 6.5 to about 8.8. More preferably, the water has a pH of from about 7 to 8, and most preferably from about 7.2 to about 7.6. The buffering of the pool water pH in this near-neutral range reduces skin and eye irritation to swimmers which may occur from contact with pool water at other, more extreme pH ranges. Buffering in this pH range also reduces scaling and metal corrosion within the pool. Thus this pH range is believed to be generally ideal for the operation and maintenance of the pool.

As a further advantage, buffering at this pH range is believed to aid in the retention of dissolved chlorine and to improve the disinfectant properties of any supplemental chlorine-based sanitizer due to the balance between free available chlorine and hypochlorous acid which occurs at this pH range.

In certain embodiments, the pH buffering action is believed to derive substantially entirely from the borate salt and the sanitizer without the need for additional pH adjustment chemicals such boric or other acids (such as hydrochloric acid) or alkaline bases.

The properties and advantage of the present disclosure are illustrated in further detail in the following nonlimiting examples. Unless otherwise indicated, temperatures are expressed in degrees Celsius, concentrations of the algaecidal buffer are expressed in weight %, and concentration of free chlorine are expressed in parts per million (ppm).

Example 1

Borate Biostat Buffer Dissolution Tests

In this example, different forms of borates were added to columns of water and a swimming pool to determine their comparative dispersion and rate of dissolution characteristics. The borate forms compared included disodium octaborate tetrahydrate, boric acid, sodium tetraborate (borax), and a mixture of boric acid and borax.

Methodology

Two hundred and fifty (250) ml of deionized water was placed in each of 4 measuring cylinders to give a 300 mm vertical column of water in each cylinder to mimic in small scale the depth of water in a swimming pool. To each column was added 0.2 g (0.08 weight %) of either boric acid (obtained commercially as OPTIBOR from U.S. Borax, Inc. of Valencia, Calif.), borax pentahydrate (obtained commercially as NEOBOR from U.S. Borax, Inc. of Valencia, Calif.), disodium octaborate tetrahydrate (obtained commercially as POLYBOR from U.S. Borax, Inc. of Valencia, Calif.) or a mixture made of 0.1 g boric acid with 0.1 g borax. The results of the addition were then observed visually and recorded.

Following this initial experiment in the lab, the same test was repeated at the shallow end of a 10,000 gallon domestic swimming pool with an addition of 5 lb of each product or of the mixture.

Results

The boric acid was observed to mostly float on top of the water and did not completely dissolve after addition. The boric acid was also observed to leave an unsightly white dust on the surface of the water. The borax sank immediately to the bottom of the cylinder and formed an encrusted mass that did not dissolve within a few minutes after addition. The mixture of the boric acid and borax segregated upon contact with the water with approximately half sinking to the bottom and half floating. In contrast, the disodium octaborate tetrahydrate was observed to immediately disperse and fully dissolve in a matter of seconds and before reaching the bottom of the column The results obtained in the swimming pool tests were substantially the same as in the initial laboratory test.

Discussion and Conclusion

From the above results, it was found that when adding a borate to a swimming pool, the use of disodium octaborate tetrahydrate is far preferred to the use of boric acid, or borax, or mixtures of both boric acid and borax in terms of the rate of product dissolution and the rate at which the pool returns to its original aesthetics. It was observed from these tests that the dispersion of material throughout the pool is more rapid and more uniform with disodium octaborate than with either of boric acid or borax or mixtures of boric acid and borax.

Example 2

Effect of Disodium Octaborate Tetrahydrate as a Chlorine Stabilizer Using Lithium Hypochlorite In this example, borates, in the form or disodium octaborate tetrahydrate, were added to an aqueous solution of lithium hypochlorite in order to determine the effectiveness of disodium octaborate in stabilizing a hypochlorite pool sanitizer.

Methodology

Two glass laboratory beakers each with a capacity of 2 liters were partially filled with chlorinated deionized water (1 liter each) with or without added disodium octaborate tetrahydrate. The chlorine solutions were prepared by first dissolving 0.1 gram of lithium hypochlorite (obtained commercially as SPA TIME lithium hypochlorite) in 1 liter of deionized water. 500 ml of this resulting solution was then further diluted to 1 liter with an additional 500 ml deionized water.

The resulting solutions were measured using free chlorine indicator strips and found to contain 10 ppm of free chlorine. 0.5 grams of disodium octaborate tetrahydrate (obtained commercially as POLYBOR from US Borax) was then added to one of the beakers to obtain a 0.05 weight % disodium octaborate tetrahydrate concentration. The second beaker of chlorine solution was used as a control with no disodium octaborate tetrahydrate added. Both beakers were then immediately placed outside in bright sunlight in August at midday in Rockford, Tenn. The free chlorine content in each beaker was then measured using free chlorine indicator strips at time intervals of 0 hours, 1.5 hours, and 2.5 hours.

Results

The measured free chlorine concentrations for reach beaker and time period are tabulated below.

| Time | Control Beaker | Disodium Octaborate Tetrahydrate Beaker |
| --- | --- | --- |
| 0 hr. | 10 ppm | 10 ppm |
| 1.5 hr. | 0 ppm | 1.0 ppm |
| 2.5 hr. | 0 ppm | 0.5 ppm |

Discussion and Conclusions

These results demonstrate that the addition of disodium octaborate tetrahydrate to chlorinated water reduced the rate of photo-induced loss of free chlorine from the water. This results in an increase in the longevity of the chorine sanitizer performance and a reduction of the amount of chlorine addition required over a period of time.

While the measured free chlorine disappeared relatively quickly even from the disodium octaborate tetrahydrate treated water, the photo-degradation of the free chlorine was highly acerbated under the testing conditions used, i.e., due to the very small volume of water used in the test and the very strong sunlight on the day of the test. In a larger body of water, such as a swimming pool, and under less extreme heat and light conditions, the rate of chlorine loss in both the disodium octaborate-treated water and in the untreated water would likely be slower than the rates observed in this example. However, the rate of chlorine loss in the disodium octaborate-treated water would still be slower than in the untreated water under the same heat and light conditions. Thus, the addition of disodium octaborate was observed to provide a significant benefit in reducing chlorine loss and would provide a benefit in commercial pool treatments by prolonging the antiseptic performance of the chlorine in the pool water and reducing the amount of chlorine replenishment that needed to be added over a period of time.

Example 3

Comparison of Sodium Pentaborate and Sodium Tetraborate as Chlorine Stabilizers Using Dichlor In this example, two different borates, sodium pentaborate and sodium tetraborate (borax), were added to aqueous solutions of sodium dichloro-s-triazinetrione dihydrate ("dichlor") pool sanitizer in order to compare the relative effectiveness of the two borates in stabilizing the dichlor sanitizer.

Methodology

Two glass laboratory beakers each with a capacity of 1 liter were partially filled with chlorinated deionized water (0.5 liters each) with or without added pentaborate (sodium pentaborate) or borax (borax). The chlorine solutions were prepared by first dissolving 0.05 g of dichlor (in the form of a vinyl pool shock product available under the tradename AQUACHEM from Bio-Lab, Inc. of Lawrenceville, Ga.) in 2 liters of deionized water. 500 ml of this resulting solution was then added to the beakers.

The resulting solutions were measured using free chlorine indicator strips and found to contain 10 ppm free chlorine. 0.25 grams of sodium pentaborate (obtained commercially as SOLUBOR DF from US Borax) was then added to one of the beakers to obtain a 0.05 weight % sodium pentaborate concentration. 0.25 g of borax (obtained commercially as NEO-BOR from US Borax) was added to the other beaker to obtain a 0.05 weight % borax concentration. Both beakers were then immediately placed outside in bright sunlight at the beginning of October 2006 at 3:50 pm in Rockford, Tenn. The free chlorine content in each beaker was then measured at 0 time, 15 minutes, 30 minutes, 45 minutes 60 minutes, 80 minutes and 980 minutes.

Results

The measured free chlorine concentrations for each beaker and time period are tabulated below.

| Time | Sodium Pentaborate Beaker | Borax Beaker |
|---|---|---|
| 0 | 10 ppm | 10 ppm |
| 15 minutes | 10 ppm | 7.5 ppm |
| 30 minutes | 7.5 ppm | 3 ppm |
| 45 minutes | 5 ppm | 1 ppm |
| 60 minutes | 5 ppm | 0.5 ppm |
| 80 minutes | 3 ppm | 0 ppm |
| 980 minutes (next morning) | 1 ppm | 0 ppm |

Discussion and Conclusions

These results demonstrate that the treatment of water by addition of sodium pentaborate to chlorinated water reduces the rate of photo-induced loss of free chlorine from the water as compared to treatment of water by the addition of sodium tetraborate (borax). Thus, treatment according to the disclosure was observed to increase the longevity of chorine sanitizer performance and reduce the amount of chlorine addition required over a period of time.

While the measured free chlorine was observed to disappear relatively quickly even from the sodium pentaborate treated water, the photo-degradation of the free chlorine was observed to be highly acerbated under the testing conditions used characterized by the use of a small volume of water and strong sunlight on the day of the test. In a larger body of water, such as a swimming pool, and under less extreme heat and light conditions, the rate of chlorine loss in both the sodium pentaborate-treated water and in the borax-treated water is expected to be slower than the rates observed in this example. However, based on the observed results, the rate of chlorine loss in the sodium pentaborate-treated water would be expected to be slower than in the borax-treated water under the same heat and light conditions. Thus, the addition of sodium pentaborate according to the disclosure would provide a significant benefit in commercial pool treatments by prolonging the antiseptic performance of the chlorine in the pool water and reducing the amount of chlorine replenishment that needed to be added over a period of time.

Example 4

Comparative Example Using Lake Water

In order to compare the effectiveness of disodium octaborate tetrahydrate to sodium tetraborate (borax) in suppressing algae growth in previously untreated water, approximately 5 liters of clear lake water was collected from the Little River tributary of Lake Loudoun on the Tennessee River. From this lake sample, three 1 liter glass beakers were each filled with 900 mL of lake water. Disodium octaborate tetrahydrate was added to one beaker to provide a concentration of 0.1 weight percent disodium octaborate tetrahydrate. Sodium tetraborate was added to a second beaker to provide a concentration of 0.1 weight percent sodium tetraborate. The third beaker was left as an untreated control. The three samples, which were collected in August, were then left outside, fully exposed to the sun, for a period of two months.

After the two month period, the samples were then visually inspected for algal growth. The samples were also analyzed using a Spectronic Genesys 20 spectrophotometer from Thermo Scientific. This analysis was conducted by testing for absorbance at 330 nm.

In the visual inspection excessive algal growth was observed in the untreated sample, slight growth was observed in the borax treated sample and very minimal growth was observed in the DOT treated sample.

These findings were corroborated by the absorbance readings obtained spectrophotimetrically and given below:

| Sample | Absorbance (Abs.) |
|---|---|
| Untreated (Control) | 0.258 |
| Sodium tetraborate | 0.01 |
| Disodium octaborate tetrahydrate | 0.004 |

The higher absorbance readings in the control and the borax samples are indicative of higher algal growth in the water samples.

Example 5

Corrosiveness Comparative Example

In this example, the corrosiveness of disodium octaborate tetrahydrate was compared to that of boric acid. The test was conducted with two 500 mL beakers which were each filled with 200 mL of water (199.75 g). 0.5 grams of disodium octaborate tetrahydrate was added to the first beaker and 0.5 grams of boric acid was added to the second beaker, thus providing a 0.25 weight % solution in each beaker.

A steel framing nail was then placed in each solution and left for a period of two weeks. After the two week period, the nail in the boric acid solution was observed to be significantly corroded, and the solution was observed to have turned brown due to the presence of the corrosion product (likely iron oxide) in solution. On the other hand, the nail in the disodium octaborate tetrahydrate solution was observed to be free of significant corrosion, and the solution was observed to be clear and free of corrosion by-products.

Example 6

Use of Sodium Hexaborate as a Buffer

In this example, different borates were added to swimming pools, together with a chlorine-based sanitizer, in order to measure pH and free chlorine (CY) levels in the swimming pools over a period it time.

Three substantially identical, 2000 gallon above-ground swimming pools were used for the tests. Each pool was initially filled with approximately 2000 gallons of tap water, and then 500 milliliters of lake water was added to each pool to inoculate the pool water with algae. The testing was conducted during the month of September at a location near Knoxville, Tenn.

In the first pool, approximately 4 pounds of sodium tetraborate was added to the pool water. Approximately 4 pounds of sodium hexaborate was added to water of the second pool. The third pool was used as a control with no form of borate being added to the pool water. The borates in the first and second pools were then allowed to mix overnight.

The following morning, initial pH and chlorine measures were taken for each pool at approximately 9:45 am. Approximately 0.3 pounds of calcium hypochlorate was then added to the water in each of the three swimming pools at approximately 10 am. The pH and chlorine levels in each of the pools were then measured periodically over the course of the day. The measurements obtained were as follows:

| | Free chlorine level (ppm) for swimming pool water with: | | |
|---|---|---|---|
| Time | No borate | Sodium tetraborate | Sodium hexaborate |
| 9:45 am | 0 | 0 | 0 |
| 10:00 am | 0 | 0 | 0 |
| 10:55 am | 10 | 10 | 10 |
| 11:15 am | 10 | 10 | 10 |
| 12:00 pm | 10 | 10 | 10 |
| 12:40 pm | 10 | 10 | 10 |
| 1:25 pm | 5 | 10 | 9 |
| 2:10 pm | 3 | 5 | 6.5 |
| 2:50 pm | 1 | 0.5 | 1.5 |
| 3:30 pm | 0.5 | 0 | 0.75 |
| 4:10 pm | 0 | 0 | 0.75 |
| 5:00 pm | 0 | 0 | 0 |

| | pH for swimming pool water with: | | |
|---|---|---|---|
| Time | No borate | Sodium tetraborate | Sodium hexaborate |
| 9:45 am | 7.0 | >8.4 | 7.2-7.8 |
| 10:00 am | 7.6 | >8.4 | 7.2-7.8 |
| 10:55 am | 8.4 | >8.4 | 7.2-7.8 |
| 11:15 am | 8.4 | >8.4 | 7.8-8.4 |
| 12:00 pm | 8.4 | >8.4 | 7.8-8.4 |
| 12:40 pm | 7.8 | >8.4 | 7.8-8.4 |
| 1:25 pm | 6.8 | >8.4 | 7.2-7.8 |
| 2:10 pm | 6.8 | >8.4 | 7.2-7.8 |
| 2:50 pm | 6.8 | >8.4 | 7.2-7.8 |
| 3:30 pm | 6.8 | >8.4 | 7.2-7.8 |
| 4:10 pm | 6.8 | >8.4 | 7.2-7.8 |
| 5:00 pm | 6.8 | >8.4 | 7.2-7.8 |

These results show that the sodium tetraborate slowed the decomposition of the free chlorine to some degree as compared to the control with no borates added. However, the sodium hexaborate was more effective than the sodium tetraborate and provided the greatest reduction in the decomposition rate for the free chlorine.

In addition, the results also show that the sodium hexaborate buffered the water at a lower pH, generally in the range of from about 7.2 to about 7.8. In contrast the sodium tetraborate buffered the water at a pH in excess of 8.4, which was the maximum pH value measurable on the pH meter used during this test. The lower and more neutral pH of the sodium hexaborate buffered water would generally be more comfortable for swimming and using the pool, improve water clarity, and maximize the performance of chlorine.

In a further aspect, the present disclosure also provides a borate-based microemulsion concentrate suitable for use in the treatment of swimming pools and similar structures. In addition to water, the microemulsion product includes at least emulsified sodium pentaborate and particulate boric acid suspended therein. In general, the microemulsion product, in its concentrated form, includes from about 18 to about 38 weight percent emulsified sodium pentaborate and from about 18 to about 38 weight percent particulate boric acid. More preferably, the microemulsion concentrate includes from about 24 to about 32 weight percent emulsified sodium pentaborate and from about 24 to about 32 weight percent particulate boric acid. Thus, the microemulsion concentrate generally includes from about 8 to about 13 weight percent elemental boron. In certain embodiments, the microemulsion concentrate more preferably includes about 10 weight percent elemental boron or about 11.5 weight percent elemental boron.

In certain embodiments, the microemulsion concentrate may also include from about 0.01 to about 0.75 weight percent of an anti-settling agent selected from the group consisting of xanthan gum, polyacrylates, acrylic acid, agar, carboxymethyl cellulose, clay, and mixtures thereof.

The product is referred to as a "microemulsion" in that it includes both borate materials which are fully dissolved in the aqueous solvent and microscopic solid particles (micelles) of borate materials which are emulsified but are not fully dissolved in the water solvent. To the naked eye, the product has a milky or emulsion-like appearance; however, the solid micelles of undissolved borates are sufficiently small that the product feels smooth and free of grit or particles when touched by hand.

The result is a product which is quite viscous and has a cream like consistency. In certain embodiments, when tested using a Brookfield DV-I+ Viscometer, the viscosity of the microemulsion product has been found to generally be from about 1000 to about 2000 centipoise at a temperature of from about 64° F. to about 72° F. More preferably, the viscosity of the microemulsion product ranges from about 1200 to about 1520 centipoise at a temperature of from about 66° F. to about 70° F. However, in certain other embodiments, the microemulsion may be somewhat more viscous, having a viscosity from about 1000 to about 3000 centipoise, and more preferably from about 2000 to about 2800 centipoise, at a temperature of from about 70° F. to about 75° F.

The density of the microemulsion concentrate may range from about 9 to about 11 pounds per gallon at about room temperature, more preferably from about 9.5 to about 10.5 pounds per gallon at about room temperature. Still more preferably, the density of the microemulsion product is about 10.2 pounds per gallon at about room temperature The pH of the microemulsion product, in its concentrated form, is generally from about 6 to about 7.5 in certain embodiments. More preferably, the pH of the microemulsion concentrate is from about 6.5 to about 7. Most preferably, the pH of the microemulsion concentrate is from about 6.7 to about 6.9.

In one embodiment, the borate-based microemulsion concentrate may be prepared by mixing one part, by weight, of an acidic borate with from about 0.6 to about 1.4 parts, by weight, of an alkali borate and from about 1.5 to about 3 parts, by weight, water to form a first mixture. The first mixture is then reacted to provide a first reaction product which comprises emulsified sodium pentaborate. The first reaction product is then mixed with an additional from about 0.5 to about 4 parts, by weight, acidic borate and from about 0.5 to about 2 parts, by weight, water to provide a second product, the microemulsion concentrate, which includes both emulsified sodium pentaborate and particulate boric acid suspended therein.

Preferably, the acidic borate used in preparing the first mixture includes at least one borate selected from the group consisting of orthoboric acid, metaboric acid, boric oxide, and mixtures thereof. More preferably, the acidic borate includes a boric acid, and most preferably, the acidic borate includes orthoboric acid.

The alkali borate used in preparing the first mixture preferably includes at least one borate selected from the group consisting of sodium borates, potassium borates, lithium borates, and mixtures thereof. Sodium borates, such as tincal ($Na_2B_4O_7 \times 10\ H_2O$), kernite ($Na_2B_4O_7 \times 4\ H_2O$), anhydrous sodium tetraborate, sodium tetraborate pentahydrate, sodium tetraborate decahydrate are more preferred. Alternatively, borate minerals such as ulexite ($NaCaB_5O_9 \times 8\ H_2O$) or colemanite ($CaB_3O_4(OH)_3 \times H_2O$) may also be used. Anhydrous sodium tetraborate, sodium tetraborate pentahydrate, and sodium tetraborate decahydrate are particularly preferred, with sodium tetraborate pentahydrate being most preferred.

Once mixed, the acidic borate and the alkali borate are reacted with one another. In general, this reaction may be carried out at any temperature from about 32° F. to about 212° F. More preferably, this reaction may be carried out at a temperature of from about 40° F. to about 100° F. The reaction of the acidic borate and the alkali borate is preferably, but not necessarily, carried out in a high shear mixer or a ribbon blender such as a Saracco 3813 or a Marion BPC 4296.

Reaction of the acidic borate and the alkali borate results in the formation of a first reaction product. The first reaction product includes a substantial amount of sodium pentaborate in an emulsified form. Preferably, the first reaction product includes from about 25 to about 75 weight percent emulsified sodium pentaborate.

The first reaction product is then mixed with additional acidic borate, preferably powdered boric acid, to provide a second product, the microemulsion concentrate. This mixing step is preferably, but not necessarily, carried out using an inline mill such as a Greerco 457 SPLN.

According to another embodiment of the present disclosure, the borate-based microemulsion concentrate may be prepared in a process with only a single reaction step. In this process, the entire amounts of the acidic borate, the alkali borate, and the water are combined initially and allowed to react. Generally, one part, by weight, of an alkali borate is mixed with from about 1 to about 15 parts, by weight, of an acidic borate and from about 1 to about 20 parts, by weight, water to form a mixture. In a more preferred embodiment, one part, by weight, of an alkali borate is mixed with from about 2 to about 5 parts, by weight, of an acidic borate and from about 2 to about 10 parts, by weight, water to form a mixture. In general, the same acidic borates and alkali borates may be used in the single reaction step process as in the two reaction step process. A preferred acid borate is orthoboric acid while a preferred alkali borate is sodium tetraborate pentahydrate. Xanthan gum or a similar anti-settling agent may also be added to the mixture.

This mixture is then allowed to react to provide a microemulsion product includes emulsified sodium pentaborate and particulate boric acid suspended therein. According to this single reaction step process, the mixing and reaction of the aforementioned components is preferably carried out in mixing vessel having a recirculation loop, driven by an appropriate recirculation pump, to improve the mixing efficiency of the vessel.

In one example of the single reaction step process, the initial mixture is about 43 weight percent orthoboric acid, 14 weight percent sodium tetraborate pentahydrate, about 0.3 weight percent xanthan gum, and about 42 weight percent water. After reaction, the final product is made up about 30 weight percent emulsified sodium pentaborate and about 30 weight percent suspended particulate boric acid, along with the xanthan gum and water.

Alternatively, the borate-based microemulsion concentrate may be prepared in a process with only a single reaction step in which an alkali borate is mixed and reacted with non-borate acid. For instance, one part, by weight, alkali borate may be mixed with from about 1 to about 20 parts, by weight, of a non-borate acid and from about 1 to about 20 parts, by weight, water to form a mixture. This mixture is then reacted at a temperature of from about 32 of to about 212 of to provide a reaction product which comprises from about 18 to about 38 weight percent emulsified sodium pentaborate and from about 18 to about 38 weight percent particulate boric acid suspended therein.

In certain embodiments, the alkali borate preferably includes a borate selected from the group consisting of tincal, kernite, anhydrous sodium tetraborate, sodium tetraborate pentahydrate, sodium tetraborate decahydrate, and mixtures thereof. More preferably, the alkali borate includes sodium tetraborate pentahydrate.

In certain embodiments, the non-borate acid preferably includes an acid selected from the group consisting of sulfuric acid, sulphur dioxide, sodium bisulphate, potassium bisulphate hydrochloric acid, chlorine, hypochlorous acid, carbon dioxide, carbonic acid, phosphoric acid, and mixtures thereof. In this context, materials such as sulphur dioxide, bisulfate salts, chlorine, and carbon dioxide are considered to be acids since they yield acids when dissolved in water.

In other embodiments, the non-borate acid preferably includes an organic acid selected from the group consisting of carboxylic acids, dicarboxylic acids, sulfonic acids, and mixtures thereof. Suitable carboxylic acids include, for example, formic acid, acetic acid, and propionic acid. Suitable dicarboxylic acids include, for example, oxalic acid and succinic acid.

In still another alternative, the borate-based microemulsion concentrate may be prepared in a process with only a single reaction step in which an acidic borate is mixed and reacted with non-borate base. For example, one part, by weight, acid borate may be mixed with from about 0.05 to about 2 parts, by weight, of a non-borate base and from about 1 to about 3 parts, by weight, water to form a mixture. This mixture is then reacted at a temperature of from about 32 of to about 212 of to provide a reaction product which comprises from about 18 to about 38 weight percent emulsified sodium pentaborate and from about 18 to about 38 weight percent particulate boric acid suspended therein.

In certain embodiments, the acidic borate includes a borate selected from the group consisting of orthoboric acid, metaboric acid, boric oxide, and mixtures thereof. More preferably, the acidic borate includes orthoboric acid.

In certain embodiments, the non-borate base includes a base selected from the group consisting of sodium hydroxide, potassium hydroxide, calcium hydroxide, magnesium hydroxide, lithium hydroxide, sodium oxide, potassium oxide, calcium oxide, magnesium oxide, lithium oxide, sodium carbonate, potassium carbonate, calcium carbonate, magnesium carbonate, lithium carbonate, and mixtures thereof. More preferably, the non-borate base includes sodium hydroxide.

In other embodiments, the non-borate base may include an organic base such as a primary amine, a secondary amine, or a tertiary amine.

Once prepared, the microemulsion concentrate may be stored for long periods in a stable form without significant precipitation or solidification of the borates. It has been observed that even after a year of storage, the microemulsion concentrate is still usable and generally requires only mild shaking or agitation prior to being used to treat various water bodies such as fountains, pool sand spas.

When added to swimming pools, fountains, spas and the like, the borate microemulsion product has been found to aid in the prevention of algae growth and in the killing of pathogens, particularly when used in combination with a chlorine-based sanitizer. In addition the borate microemulsion product has been found to reduce scaling and corrosion, to reduce skin and eye irritation of bathers, to compensate for lower cyanuric acid or free chlorine concentrations in the water, to reduce necessary pump filtration times, to help water clarity and to reduce or prevent mosquito larvae development in same water bodies if abandoned and left without chlorine (e.g. after a natural disaster or after home foreclosures). Further, the microemulsion concentrate is particularly well suited for use in the treatment of swimming pools in order to buffer the pH of the pool water.

The microemulsion concentrate may be added to the swimming pool water at a ratio of from about 1000 to about 5000 gallons of water per 1 gallon of microemulsion concentrate. More preferably, the concentrate is diluted in the swimming pool water at water at a rate of about 1 gallon microemulsion per 3000 gallons water. Alternatively, the concentrate is diluted in the swimming pool water at water at a rate of about 1 gallon microemulsion per 2000 gallons water.

Addition of the microemulsion concentrate to swimming pool water in these proportions leads to an elemental boron concentration in the water of from about 10 to about 100 parts per million (ppm), more preferably from about 30 to about 80 ppm.

In certain instances, the microemulsion concentrate may be added to the swimming pool at the pool skimmer and the recirculation of the skimmer may be used to mix the concentrate with the pool water. Advantageously, it has been found that the microemulsion concentrate readily blends with the pool water in this manner and does not clog the pool skimmer or its associated piping.

As noted above, the pH of the microemulsion product, in its concentrated form, is generally from about 6 to about 7.5, preferably, from about 6.5 to about 7, and most preferably, from about 6.7 to about 6.9. Thus the concentrate is generally slightly acidic in nature.

Surprisingly, however, addition of the concentrate has been found to lead to a slightly alkaline condition in the pool water. After addition of the concentrate, the pool water has been found to typically be buffered in a pH range of from about from about 7.0 to about 8.0 after. More preferably, the pH is buffered in a range from about 7.2 to about 7.9.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for making a borate microemulsion, the method comprising the steps of:

mixing one part, by weight, acidic borate with from about 0.6 to about 1.4 parts, by weight, alkali borate and from about 1.5 to about 3 parts, by weight, water to form a first mixture;

reacting the first mixture at a temperature of from about 32° F. to about 212° F. to provide a first reaction product which comprises emulsified sodium pentaborate; and mixing the first reaction product with an additional from about 0.5 to about 4 parts, by weight, acidic borate and from about 0.5 to about 2 parts, by weight, water to provide a second product which comprises emulsified sodium pentaborate and particulate boric acid suspended therein wherein the acidic borate comprises a borate selected from the group consisting of orthoboric acid, metaboric acid, boric oxide, and mixtures thereof and wherein the alkali borate comprises at least a sodium borate.

2. The method of claim 1, wherein the alkali borate comprises a borate selected from the group consisting of tincal, kernite, anhydrous sodium tetraborate, sodium tetraborate pentahydrate, sodium tetraborate decahydrate, and mixtures thereof.

3. The method of claim 1, wherein the alkali borate comprises at least ulexite.

4. The method of claim 1, wherein the second product comprises from about 18 to about 38 weight percent emulsified sodium pentaborate and from about 18 to about 38 weight percent particulate boric acid.

5. The method of claim 1, wherein the second product comprises about 10 weight percent elemental boron.

6. The method of claim 1, wherein the second product has a viscosity of from about 1000 to about 3000 centipoise at a temperature of from about 70° F. to about 75° F.

7. The method of claim 1, wherein the second product has a viscosity of from about 2000 to about 2800 centipoise at a temperature of from about 70° F. to about 75° F.

8. The method of claim 1, wherein the second product has a density of from about 9 to about 11 pounds per gallon at about room temperature.

9. The method of claim 1, wherein the second product has a pH of from about 6 to about 7.5.

10. The method of claim 1, wherein the second product has a pH of from about 6.5 to about 7.

11. A method for making a borate microemulsion, the method comprising the steps of:

mixing one part, by weight, boric acid with from about 0.6 to about 1.4 parts, by weight, sodium tetraborate and from about 1.5 to about 3 parts, by weight, water to form a first mixture;

reacting the first mixture at a temperature of from about 40° F. to about 100° F. to provide a first reaction product which comprises emulsified sodium pentaborate; and mixing the first reaction product with an additional from about 0.5 to about 4 parts, by weight, boric acid and from about 0.5 to about 2 parts, by weight, water to provide a second product which comprises emulsified sodium pentaborate and particulate boric acid suspended therein.

12. The method of claim 11, wherein the sodium tetraborate comprises sodium tetraborate pentahydrate.

13. The method of claim 11, wherein the boric acid comprises orthoboric acid.

14. The method of claim 11, wherein the second product has a density of about 10.2 pounds per gallon at about room temperature.

15. The method of claim 11, wherein the second product has a pH of from about 6.7 to about 6.9.

16. A method for making a borate microemulsion, the method comprising the steps of:

mixing one part, by weight, alkali borate with from about 1 to about 15 parts, by weight, acidic borate and from about 1 to about 20 parts, by weight, water to form a mixture; and reacting the mixture at a temperature of from about 32° F. to about 212° F. to provide a reaction product which comprises emulsified sodium pentaborate and particulate boric acid suspended therein wherein the acidic borate comprises a borate selected from the group consisting of orthoboric acid, metaboric acid, boric oxide, and mixtures thereof and wherein the alkali borate comprises at least a sodium borate.

17. The method of claim 16, wherein the alkali borate comprises a borate selected from the group consisting of tincal, kernite, anhydrous sodium tetraborate, sodium tetraborate pentahydrate, sodium tetraborate decahydrate, and mixtures thereof.

18. The method of claim 16, wherein the alkali borate comprises at least ulexite.

19. The method of claim 16, wherein the reaction product comprises from about 18 to about 38 weight percent emulsified sodium pentaborate and from about 18 to about 38 weight percent particulate boric acid.

20. The method of claim 16, wherein the reaction product comprises about 10 weight percent elemental boron.

21. The method of claim 16, wherein the reaction is carried out in a mixing vessel with a recirculation loop.

22. The method of claim 1, wherein the alkali borate further comprises a borate selected from the group consisting of potassium borates, lithium borates, and mixtures thereof.

23. The method of claim 16, wherein the alkali borate further comprises a borate selected from the group consisting of potassium borates, lithium borates, and mixtures thereof.

* * * * *